United States Patent [19]

Komai et al.

[11] Patent Number: 5,218,555
[45] Date of Patent: Jun. 8, 1993

[54] METHOD FOR JUDGING A COLOR DIFFERENCE USING RULES FUZZY INFERENCE AND APPARATUS THEREFOR

[75] Inventors: Shigeru Komai; Takayuki Horino; Yozo Yamada, all of Otsu, Japan

[73] Assignee: Toyo Boseki Kabushiki Kaisha, Japan

[21] Appl. No.: 618,564

[22] Filed: Nov. 27, 1990

[30] Foreign Application Priority Data

Nov. 27, 1989 [JP] Japan ................... 1-308192

[51] Int. Cl.$^5$ .................................. G01J 3/46
[52] U.S. Cl. ........................... 364/526; 395/900
[58] Field of Search ............. 364/526; 395/900; 356/405, 408, 425, 443; 8/400; 358/75, 80; 354/20; 250/226

[56] References Cited

U.S. PATENT DOCUMENTS 4,901,254 2/1990 Dolezalek et al. ............ 364/526
5,089,977 2/1992 Pflasterer et al. ............. 364/526

FOREIGN PATENT DOCUMENTS 62-142241 6/1987 Japan .
62-289738 12/1987 Japan .
63-36136 2/1988 Japan .
63-235832 9/1988 Japan .

OTHER PUBLICATIONS

Cantrell; "Chips for artificial intelligence"; Circuit cellar ink Jun./Jul. 1990.

*Primary Examiner*—Parshotam S. Lall
*Assistant Examiner*—Ellis B. Ramirez
*Attorney, Agent, or Firm*—Wegner, Cantor, Mueller & Player

[57] ABSTRACT

Method for judging a color difference between a color of an object and a reference color and apparatus therefor in which it is judged at first if the color difference exists within a predetermined range in which it is difficult to determine whether or not the color difference is definite and, if it exists within the predetermined range, the color difference is judged whether it is substantial or nealigible according to rules according to Fuzzy inference.

14 Claims, 10 Drawing Sheets

FIG. 6a $$\begin{cases} 10 \leq L \leq 30 \\ 0 \leq a \leq 10 \\ -20 \leq b \leq 0 \end{cases}$$

FIG. 9c $\square APDCB = \alpha - \alpha/4 = 3\alpha/4$ $\triangle APB + \triangle DPC = \alpha/2$ $\therefore$ Credibility $= \dfrac{\alpha/2}{3\alpha/4} \fallingdotseq 0.667$

METHOD FOR JUDGING A COLOR DIFFERENCE USING RULES FUZZY INFERENCE AND APPARATUS THEREFOR

BACKGROUND OF THE INVENTION

1. Field of the Invention

The present invention relates to a method for judging color of an object (the color difference) using a color camera or a color sensor and an apparatus therefor.

2. Description of Related Art

Various color judging methods using a color camera or sensor have been developed. For example, there has been known a binary color difference judgment wherein a color difference between an object and a reference sample is measured, the measured color difference is compared with a predetermined value and a judgment in two ways of OK and NO is made according to the result of comparison.

However, such a simple method as mentioned above often fails in obtaining a credible judgment with a high accuracy since the color of an object accompanies with a certain vagueness. This is especially true in such a case that a delicate color difference due to dyeing specks of cloth or between respective lots of cloth is to be judged.

Accordingly, in such a case, the visual examination by an expert is done actually to guarantee the credibility in the color difference judgment.

However, the visual examination includes variety due to personal difference and/or time series resulting in insufficient credibility and stability.

SUMMARY OF THE INVENTION

One object of the present invention is to provide method and apparatus for judging color difference with excellent uniformity and credibility.

Another object of the present invention is to provide method and apparatus wherein judgment is done in response to the degree of a color difference detected.

To accomplish these objects, according to the present invention, there is provided a method for comparing a color of an object with a reference color having measured beforehand and judging a color difference between two colors which comprises, step for measuring said color of an object, step for calculating a color difference between said color of an object and said reference color, step for determining whether or not said color difference exists within a predetermined range in which it is difficult to determine if said color difference is definite or negligible, and step for fudging whether or not said color difference is substantial, when it exists within said predetermined range, with use of Fuzzy inference.

According to the present invention, manners and knowhow for judging the color difference by experts are taken into rules by Fuzzy inference and, therefore, the accuracy and the credibility in the automatic judgment of the color.difference are highly enhanced.

According to one aspect of the present invention, the predetermined range is determined in relation to the reference color using rules based on Fuzzy inference. This aspect can improve the accuracy and the credibility of the judgment of the color difference much more since the rules for the judgment are set in the best manner according to the color of an object to be compared with the reference color.

BRIEF DESCRIPTION OF THE DRAWINGS

These and other objects and features of the present invention will become clear from the following description taken in conjunction with the preferred embodiment thereof with reference to the accompanying drawings, in which.

DETAILED DESCRIPTION OF THE PREFERRED EMBODIMENT

First Preferred Embodiment

Figure 1:
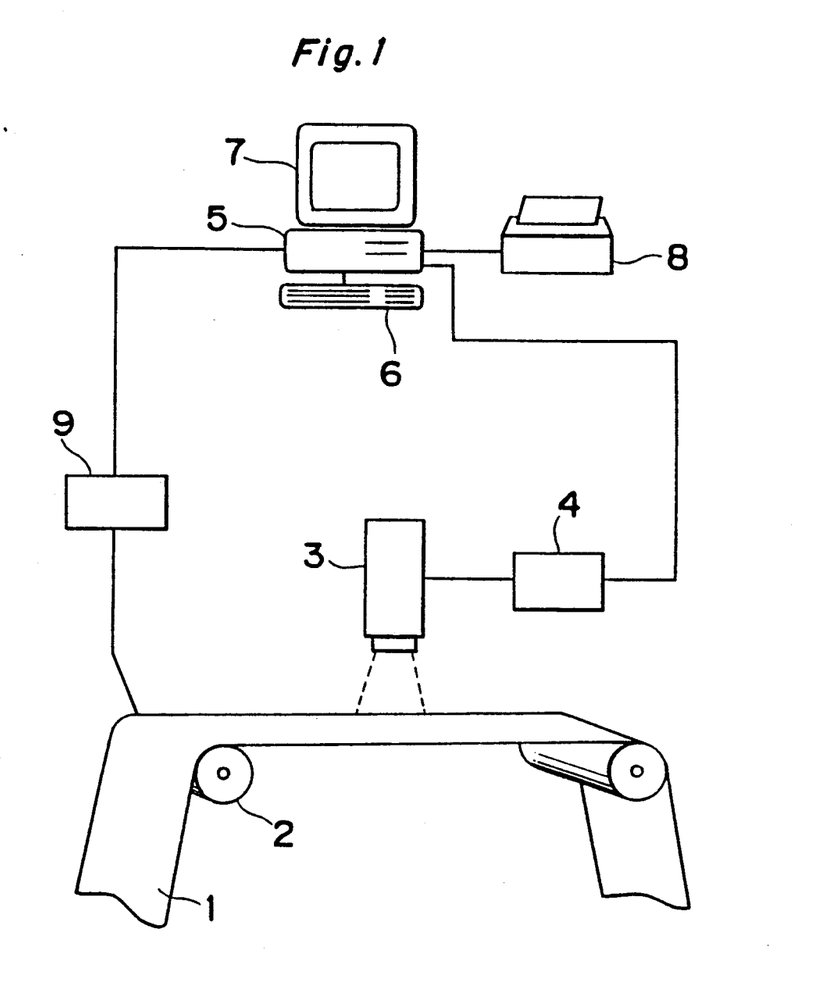
FIG. 1 shows a schematic composition of the system for judging the color difference according to the present invention.

FIG. 1 shows a system composition of an on-line color difference judging apparatus according to the present invention.

A textile fabrics 1 to be inspected is conveyed between two rollers 2 and color information thereof is detected by a color camera 3 or sensor arranged between two rollers 2. The color information detected is inputted, via an interface circuit 4, to a CPU 5. At this stage, voltage signals outputted from the color camera 3 are transformed into values in a color specification space defined for representing color quantitatively.

In this preferred embodiment, CIE Lab color specification system is used.

To the CPU 5, a key board 6, a display 7 and a printer 8 are connected. The CPU 5 also controls, via a driving circuit 9, conveyor rollers 2.

The system may provide a warning device such as a buzzer or a warning lamp activated when an abnormal color difference is detected and a memory disk apparatus for storing data.

Figure 2:
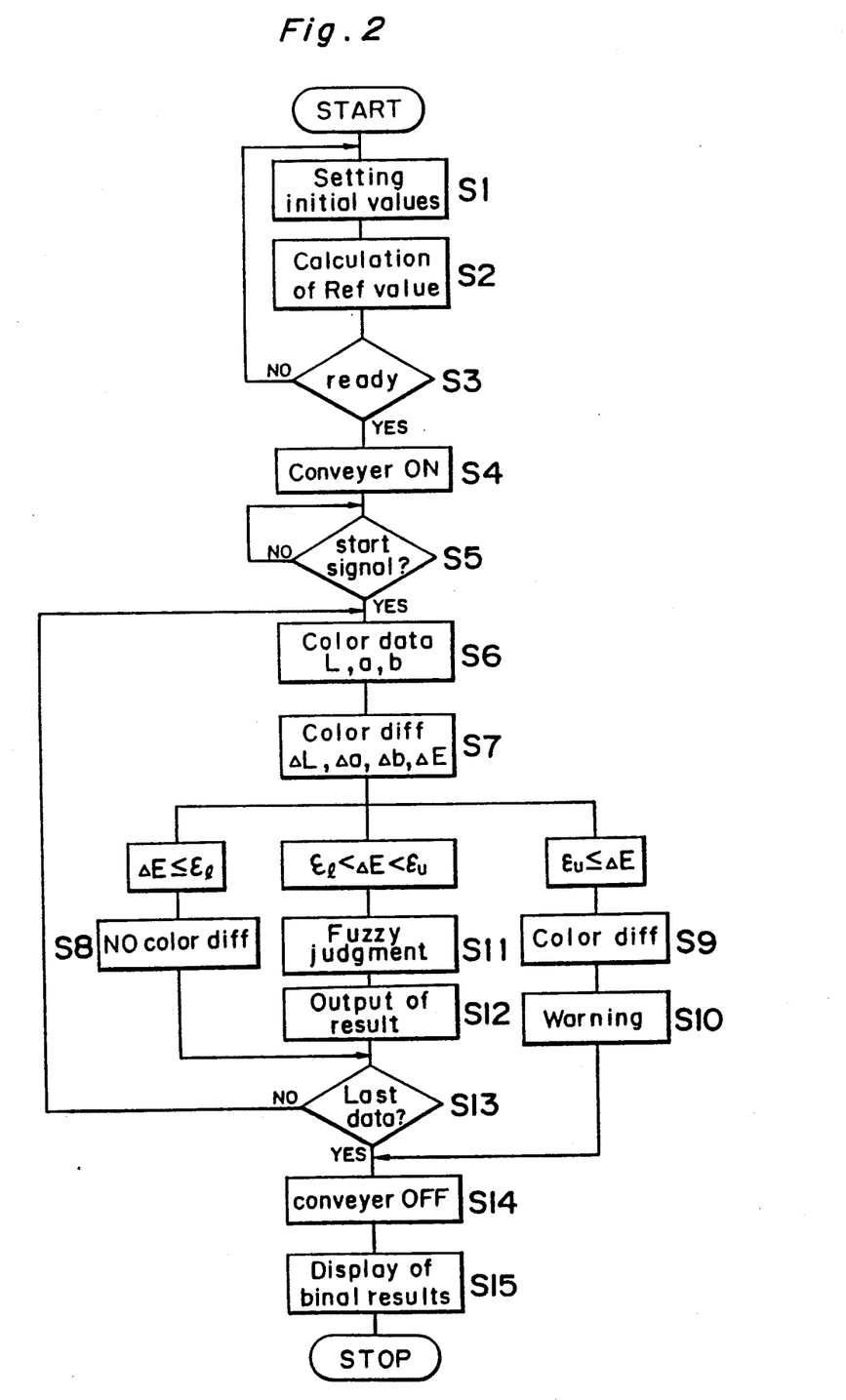
FIG. 2 shows a flow chart of the color difference judgment to be executed by CPU of the system.
Figure 3A:
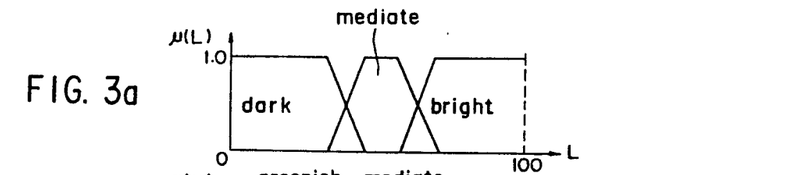
FIG. 3 shows membership functions for calculating a reference value to be used for determining whether or not the judgment of the color difference is to be done using Fuzzy inference.
Figure 3B:
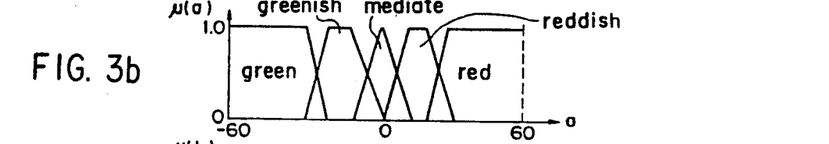
Figure 3C:
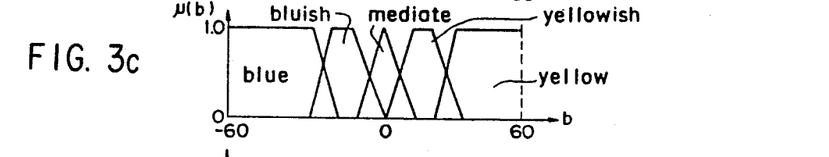
Figure 3D:
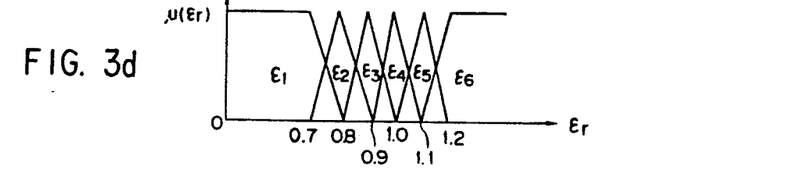
Figure 3E:
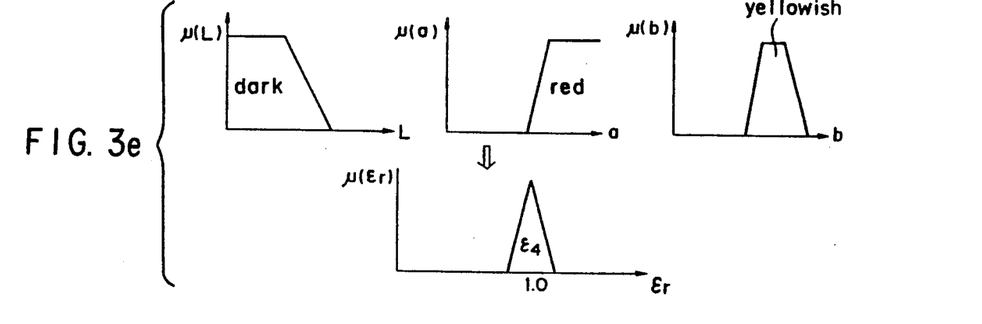
Figure 4A:
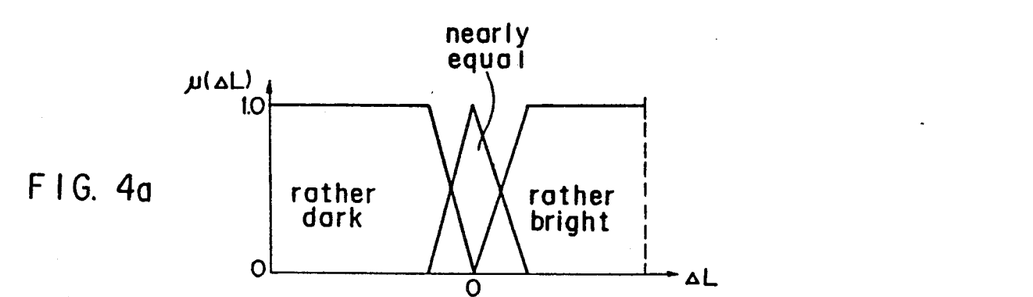
FIG. 4 shows membership functions for judging the color difference according to the first preferred embodiment of the present invention.
Figure 4B:
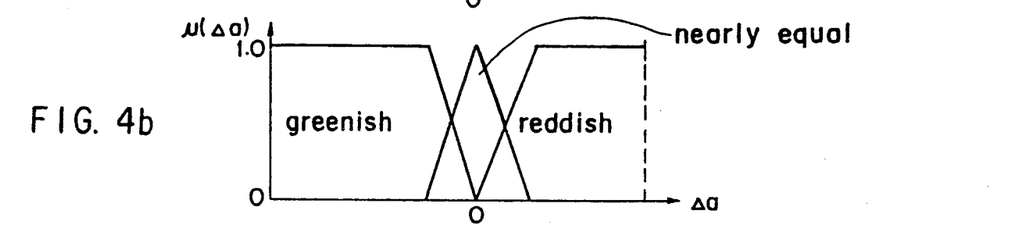
Figure 4C:
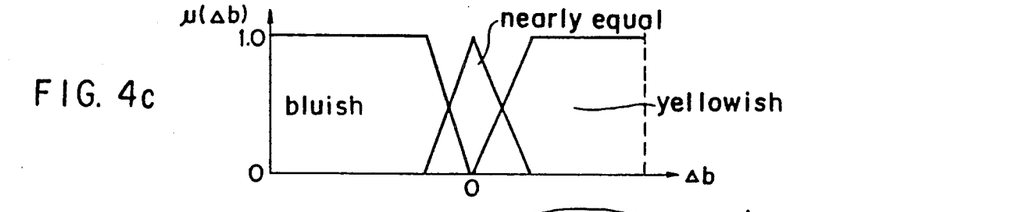
Figure 4D:
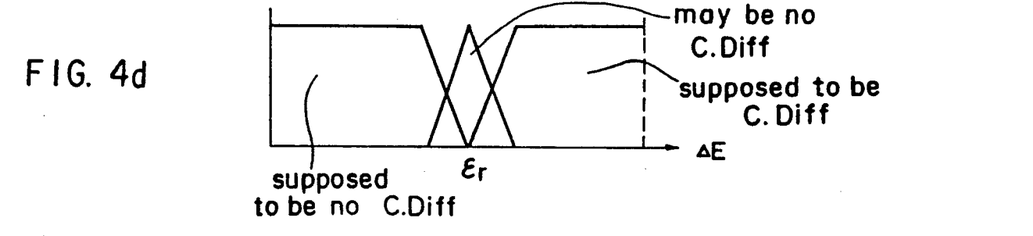

FIG. 2 shows a flow chart of the color difference judgment to be executed by the CPU 5. When the system is activated by operating a power switch, the CPU 5 is initialized at step S1.

In this initialization, Lab color specification system is selected and values $L_0$, $a_0$, $b_0$ of a reference color are inputted through the key board 6 in a reference color data input mode. Thereafter, when a measuring mode is selected at step S1, a reference value $\epsilon_r$ for judging a color difference is calculated based on the values $L_0$, $a_0$, $b_0$ having been entered at step S2. This calculation is done according to Fuzzy inference which will be explained in detail later.

As is apparent experientially, sensitivity to the color difference is different according to a color region wherein it is judged. For example, in red family color and blue family color, the reference value for judging the color difference is different from each other. Namely, the reference value should not be uniform in Lab color space and, accordingly, it should be altered based on the data of the reference color.

Determination of the reference value for judging the color difference should also be altered according to conditions other than color, for instance, kind and use of an object to be inspected and personal difference in the sensitivity of a person who judges the color difference finally.

In the present invention, Fuzzy set is introduced to take various factors mentioned above into consideration so as to be able to judge the color difference in a manner taken by an experienced inspector. Namely, know-how and experiences of the experienced inspector are represented by a membership function and the reference value for judging the color difference is calculated by Fuzzy inference using the membership function.

FIG. 3 shows four membership functions $\mu(L)$, $\mu(a)$, $\mu(b)$ and $\mu(\epsilon_r)$. From these membership functions, rules are formulated as follows. The general form of the rule is $\{IF\ \mu(L)\ is\ Li,\ \mu(a)\ is\ ai,\ \mu(b)\ is\ bi;\ THEN\ \epsilon_r\ is\ \epsilon_i\}_i, N=1$.

For instance, $\{IF\ \mu(L)\ is\ dark,\ \mu(a)\ is\ red,\ \mu(b)\ is\ yellowish;\ THEN\ \epsilon_r\ is\ \epsilon_4\}$, as shown in (e) of FIG. 3.

The reference value $\epsilon_r$ determined by these rules is used for determining lower and upper limits $\epsilon_l$ and $\epsilon_u$ between which a range for judging the color difference using Fuzzy inference is are determined by equations $\epsilon_l = \epsilon_r - \Delta\epsilon_r$ and $\epsilon_u = \epsilon_r + \Delta\epsilon_r$, respectively wherein $\Delta\epsilon_r$ is $K.\epsilon_r$ ($K<1.0$).

When it is confirmed that the system is ready for measuring the color difference at step S3, power for conveying the textile fabrics is switched on at step S4. When a start signal for measurement is inputted at step S5, color data L, a and b of the textile fabrics to be inspected are inputted at step S6. Then, at step S7, color difference data $\Delta L$ ($=L-L_0$), $\Delta a$ ($=a-a_0$) and $\Delta b$ ($=b-b_0$) and the absolute value $$\Delta E (= \sqrt{(\Delta L)^2 + (\Delta a)^2 + (\Delta b)^2}$$

are calculated at step S7.

If $\Delta E \leq \epsilon_l$, it is judged that there is no substantial color difference at step S8.

If $\Delta E \leq \epsilon_u$, it is judged that there is substantial color difference at step S9 and a warning is made by the warning device at step S10.

If $\epsilon_l < \Delta E < \epsilon_u$, the judgment of the color difference is made using Fuzzy inference at step 11.

FIG. 4 shows four membership functions $\mu(\Delta L)$, $\mu(\Delta a)$, $\mu(\Delta b)$ and $\mu(\Delta E)$.

Rules are also defined as follows. $\{IF\ \mu(\Delta L)\ is\ \Delta Li, \mu(\Delta a)\ is\ \Delta ai, \mu(\Delta b)\ is\ \Delta bi;\ THEN\ \mu(\Delta E)\}_i, N=1$.

The membership function $\mu(\Delta E)$ for judging the color difference finally is defined in three ways, for example, it seems that there is no color difference; it seems that there is not substantial color difference although there exists a small color difference and it seems that there is a significant color difference.

Since each of three membership functions $\mu(\Delta L)$, $\mu(\Delta a)$ and $\mu(\Delta b)$ is defined in three ways, twenty seven rules are defined in sum; for instance IF $\mu(\Delta L)$ is rather bright;
  $\Delta a$ is nearly equal; and
  $\Delta b$ is nearly equal,
  THEN there is no significant color difference.

Figure 5:
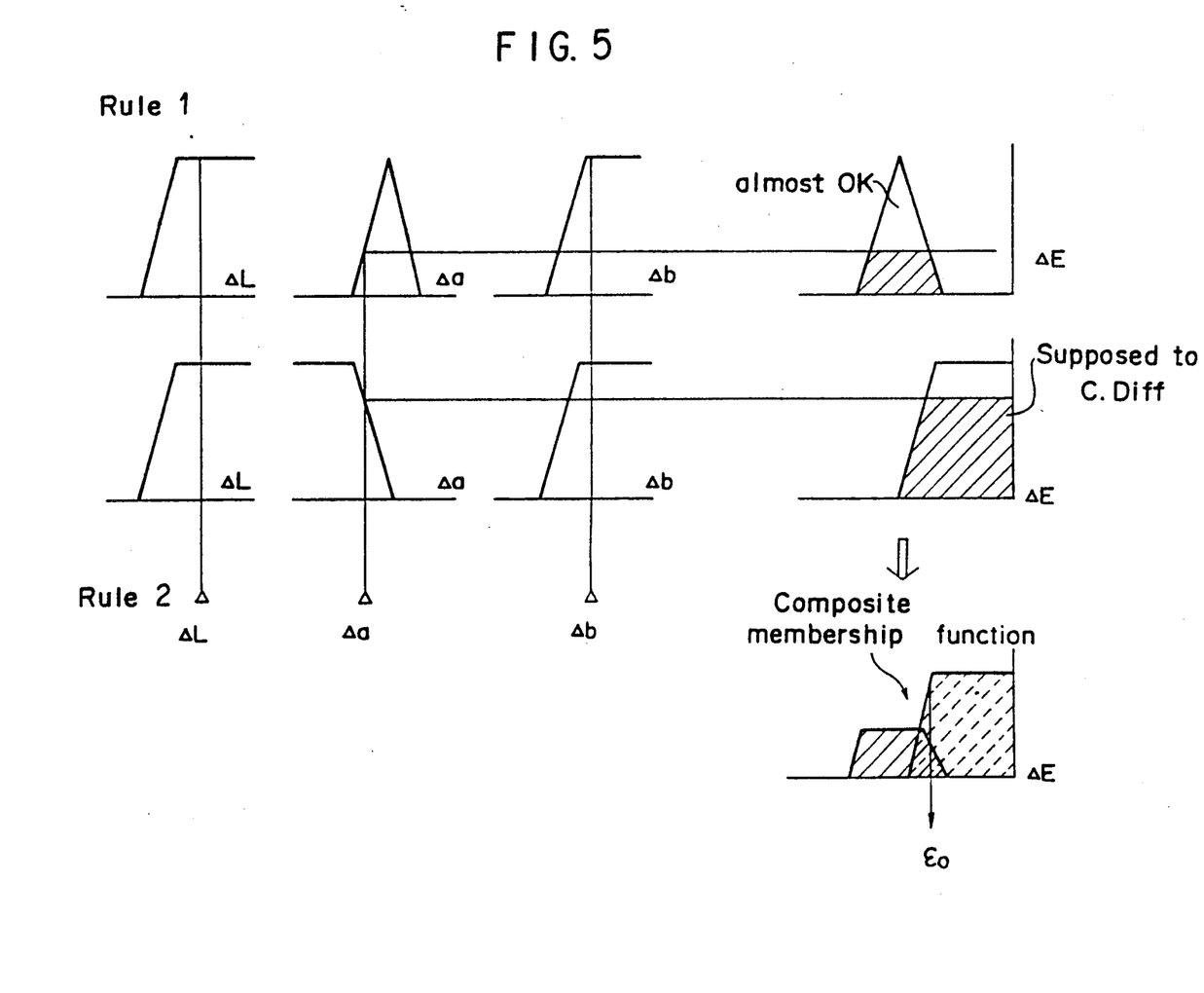
FIG. 5 shows rules for selecting the most probable rule among rules formulated using membership functions shown in FIG. 4.

FIG. 5 shows a method for selecting or determining the most probable rule among 27 rules mentioned above. In this preferred embodiment, so called direct method is used for the method.

In order for that, there are provided two rules ① and ② to be selected according to values of $\Delta L$, $\Delta a$ and $\Delta b$. Head cut of THEN proposition is done according to grade values of $\Delta L$, $\Delta a$ and $\Delta b$ to obtain respective membership functions according to the rules ① and ②. From these membership functions, a membership function is composited and, then, the center of gravity $\epsilon_0$ is calculated from the composite membership function. The Fuzzy set having the highest grade of the membership function to which the center of gravity $\epsilon_0$ is found out to determine the color difference. In the example shown in FIG. 5, since the center of gravity $\epsilon_0$ belongs to the Fuzzy set indicating that there is a significant color difference.

This final judgment is outputted at step S12 of FIG. 2.

This judgment process is repeated until it is confirmed that the final data has been treated with at step S13.

When the final data is confirmed or a warning is made, the rollers are turned off at step S14 and final results are displayed and/or printed out at step S15.

The color difference judging system according to the present invention is checked experimentally. Hereinafter, the experiment having been made will be explained.

The color sensor used in the experiment was a colorimeter CR-210 offered by Minolta and a textile fabrics of blue color for men's suits was selected since it needs a fine color difference judgment.

Data regarding samples having been judged beforehand were collected and membership functions for judging the color difference were formed.

Figure 6A:
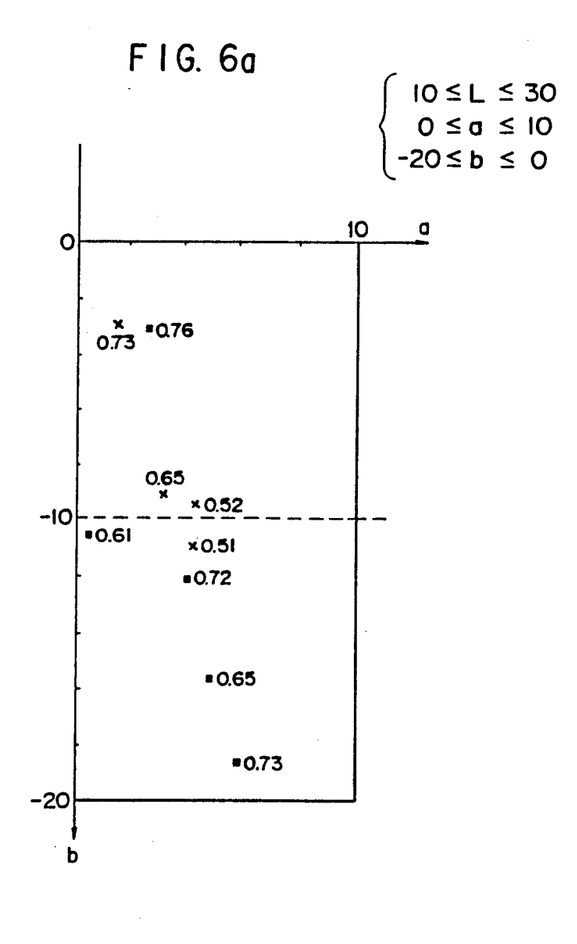
FIG. 6 shows color data related to samples of dark blue family.
Figure 6B:
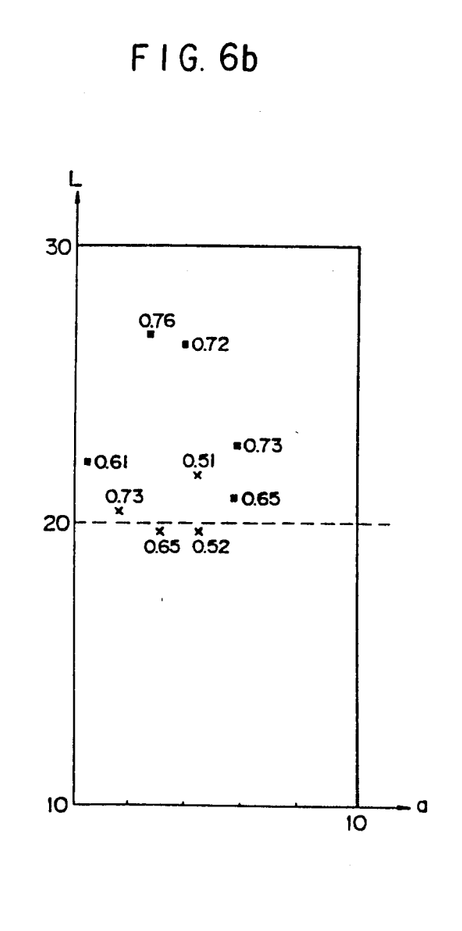
Figure 7A:
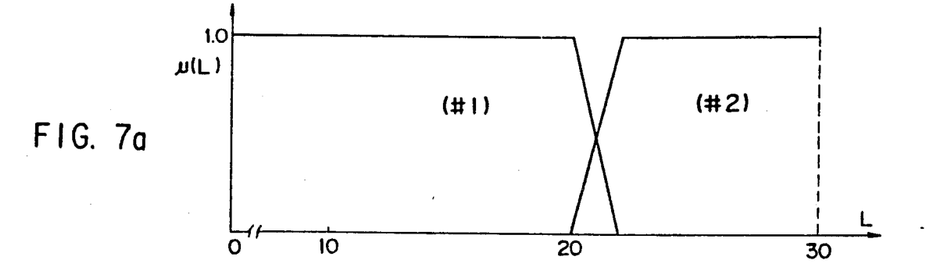
FIG. 7 shows membership functions formulated in relation to the color data shown in FIG. 6.
Figure 7B:
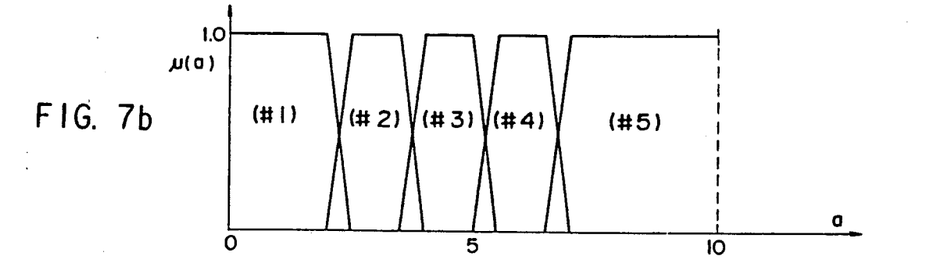
Figure 7C:
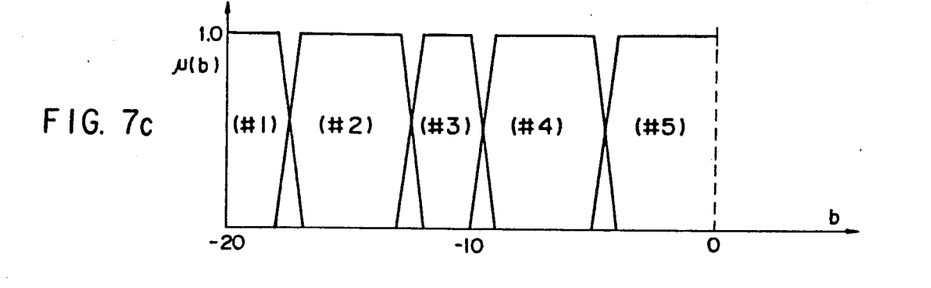
Figure 7D:
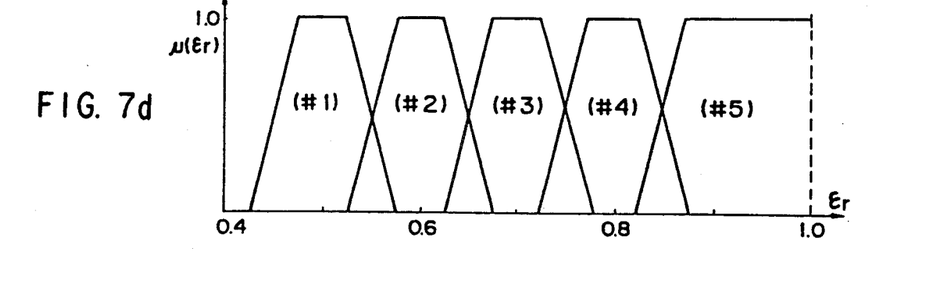
Figure 8A:
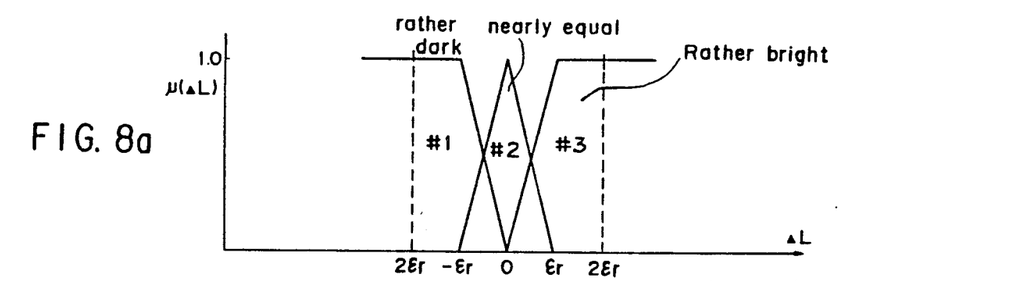
FIG. 8 shows membership functions formulated to judge the color difference using the above sample data.
Figure 8B:
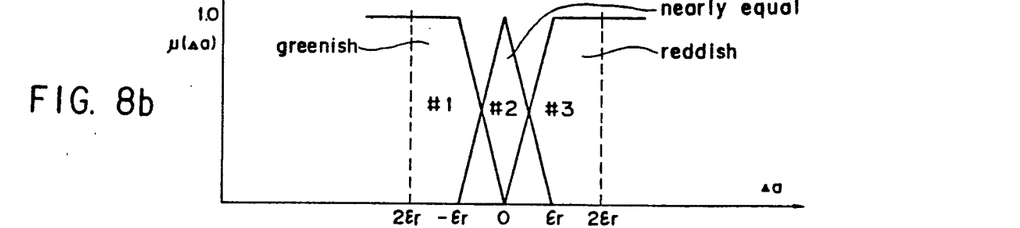
Figure 8C:
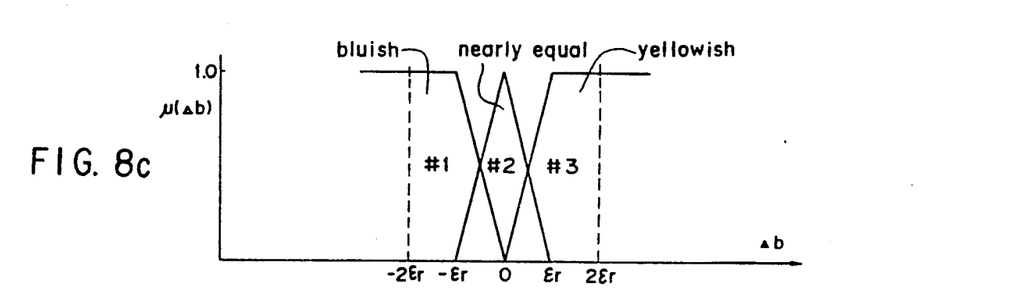
Figure 8D:
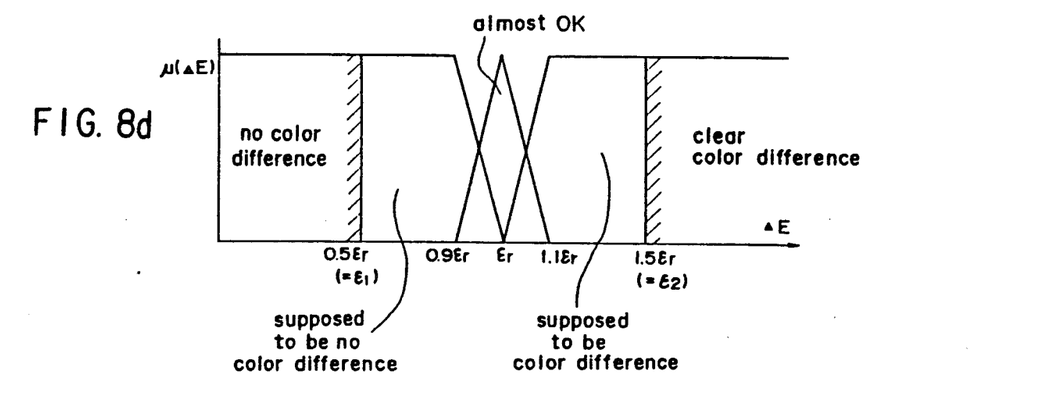

FIG. 6 shows sampled data wherein the graph (a) is represented by a-b plane and the graph (b) is represented by a-L plane.

FIG. 7 shows membership functions $\mu(L)$, $\mu(a)$, $\mu(b)$ and $\mu(\epsilon_r)$ formed by these data and rules as explained in relation to FIG. 4 using these membership functions.

In FIG. 7, respective numbers represent respective Fuzzy sets defined as follows;
$\mu(L)$;
1 very dark, #2 relatively dark
$\mu(a)$;
1 nonchromatic color,
2 near to nonchromatic color,
3 slightly reddish,
4 relatively reddish,
5 reddish
$\mu(b)$;
1 green,
2 near to green,
3 relatively green,

4 relatively near to nonchromatic color,
5 near to nonchromatic color
$\mu(\epsilon_r)$;
1 about 0.5, #2 about 0.6,
3 about 0.7, #4 about 0.8,
5 larger than or equal to 0.9.

Father, FIG. 8 shows membership $\mu(\Delta L)$, $\mu(\Delta a)$, $\mu(\Delta b)$ and $\mu(\Delta E)$ for judging the color difference. The lower and upper limits $\epsilon_l$ and $\epsilon_u$ are defined from the reference value $\epsilon_r$ obtained by Fuzzy inference.

Satisfactory results of nearly 100% was obtained in the case that the reference value $\epsilon_r$ was calculated by Fuzzy inference. This was checked with use of sampled data as input data. Values obtained by Fuzzy inference for judging the color difference coincided with results judged by the expert.

Figure 9A:
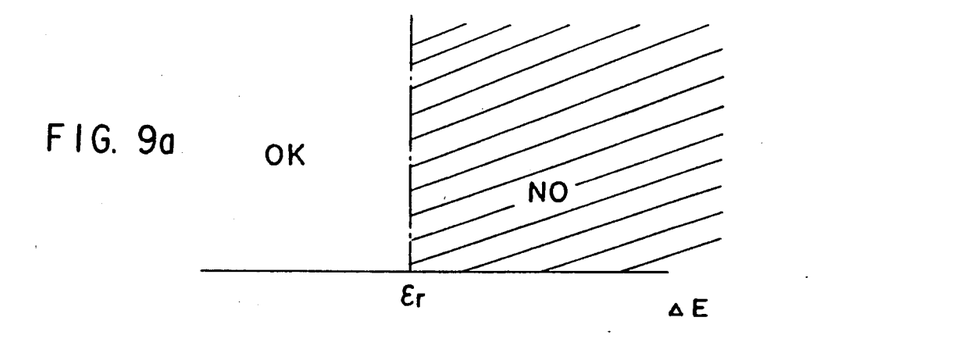
FIG. 9 shows explanatory views for indicating the credibility in the conventional method and the method according to the present invention.
Figure 9B:
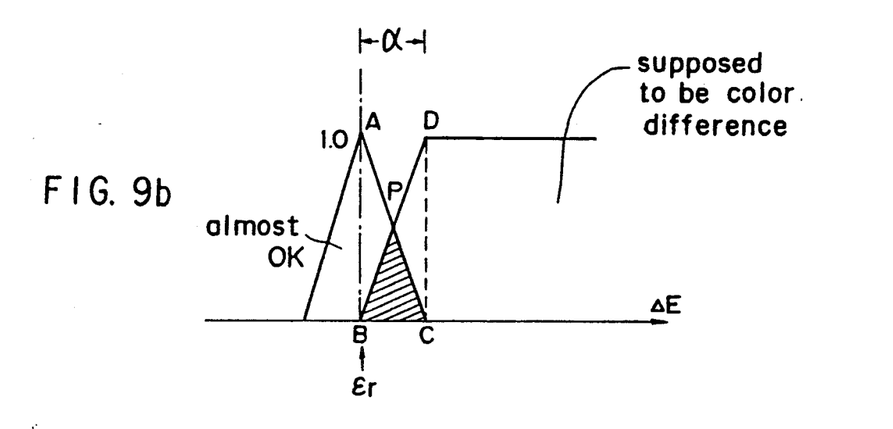
Figure 9C:
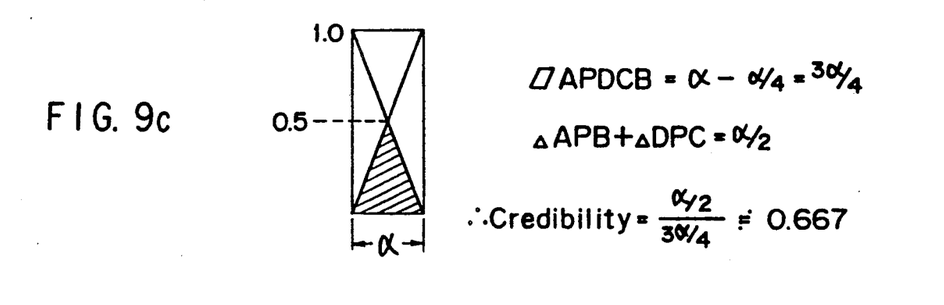

FIG. 9 shows explanatory graphs for explaining the credibility in the conventional binary judging method and in the judging method according to the present invention.

The graph (a) indicates the conventional judging method and the graph (b) indicates the judging method by the present invention.

In the conventional method, the color difference is judged only by the reference value $\epsilon_r$. Accordingly, the judgment of the color difference near the reference value is considered to be made at a credibility of 50% from the theory of probability. Also, in the method according to the present invention, the final judgment is made with use of two Fuzzy sets that it seems there is no substantial color difference and it seems there is a significant color difference.

If the color difference obtained locates in an area defined by a triangular PBC, it becomes impossible to judge definitely. But it is possible to judge definitely if it locates in either of areas defined by triangulars APB and DPC.

Therefore, the credibility in the judgment is given by a ratio as follows;

$= (\Delta APB + \Delta DPC)/_M APDCB$ $= $ (Area wherein the judgment is made exactly)
/(Whole area of grade in which points on the line segment BC locate).

In the preferred embodiment, the grade value at point P is set at 0.5 and, therefore, the credibility becomes 0.666 (66.7%) which is larger than that by the conventional method. If the membership functions were defined so as to minimize the triangular $\Delta PBC$, the credibility might be improved much more.

Second Preferred Embodiment

In this preferred embodiment, another model is employed for formulating rules for Fuzzy inference.

Figure 10:
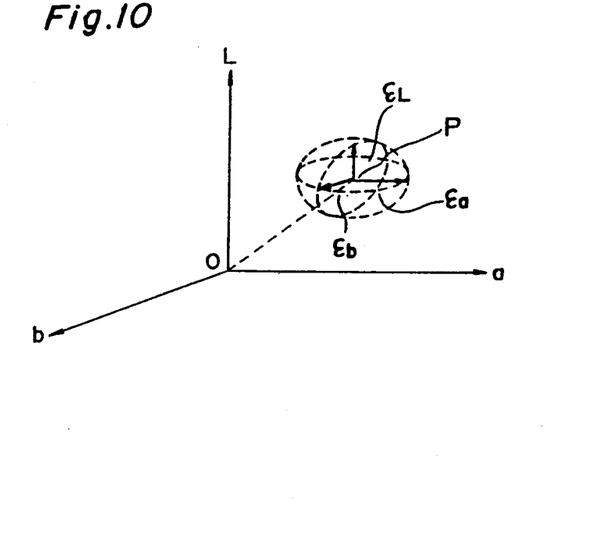
FIG. 10 shows another model employed in the second preferred embodiment of the present invention.

The expert judges the color difference in such a manner that a color of an object seems to be rather reddish or rather bright and yellowish when compared with the reference color. This manner corresponds to the judgment using L*a*b* color space (CIE 1976 L*a*b* space). Namely, each of color data L*, a* and b* of a color of an object is compared with each of color data L*, a* and b* to check whether or not the former is within a tolerance defined by $\pm\epsilon_L$, $\pm\epsilon_a$ or $\pm\epsilon_b$ (L*, a* and b* are within $(L_0^* \pm \epsilon_L)$, $(a^* \pm \epsilon_a)$ and $(b^* \pm \epsilon_b)$, respectively. In other words, reference values $\epsilon_L$, $\epsilon_a$ and $\epsilon_b$ are decided to every axis of L*, a* and b* and, as shown in FIG. 10, if the measured color locates within a partial color space (elliptic body) defined by $\epsilon_L$, $\epsilon_a$ and $\epsilon_b$ and the color data $L_0^*$, $a_0^*$ and $b_0^*$, it is judged that there is no color difference. If it locates out of the partial color space, it locates out of the partial color space, it is judged that there is a significant color difference.

In this case, it becomes necessary to obtain or calculate three reference values $\epsilon_L^*$, a* and b* axe and, accordingly, three rules are defined as follows;
{IF L* is Li, a* is ai, b* is bi; THEN $\epsilon_L$ is $\epsilon_{Li}\}_i^N = 1$,
{IF L* is Li, a* is ai, b* is bi; THEN $\epsilon_a$ is $\epsilon_{ai}\}_i^M = 1$, and
{IF L* is Li, a* is ai, b* is bi; THEN $\epsilon_b$ us $\epsilon_{bi}\}_i^P = 1$,
(wherein N, M, P are integers).

Thus, each of the reference values is calculated in such a manner as mentioned in relation to FIG. 3 of the first preferred embodiment.

Next, the method for judging the color difference when data $\Delta L$, $\Delta a$, $\Delta b$ and $\Delta E$ are obtained is explained.

Rules therefore are defined as follows;
{IF $\Delta L$ is $\Delta Li$, $\Delta E$ is $\Delta Ei$; THEN f is fi$\}_i^N = 1$,
{IF $\Delta a$ is $\Delta ai$, $\Delta E$ is $\Delta Ei$; THEN f is fi$\}_i^M = 1$, and
{IF $\Delta b$ is $\Delta bi$, $\Delta E$ is $\Delta Ei$; THEN f is fi$\}_i^P = 1$,
wherein $$\Delta L = L^* - L_0^*, \Delta a = a^* - a_0^*, \Delta b = b^* - b_0^*,$$

$$\Delta E = \sqrt{(\Delta L)^2 + (\Delta a)^2 + (\Delta b)^2} \text{ and}$$

f is an index used for judging whether or not there is a color difference.

These rules are introduced to check whether or not the measured point locates in the elliptic space defined by $\epsilon_L$, $\epsilon_a$ and $\epsilon_b$ even if each of the color data L*, a* and b* satisfies each condition, namely $\Delta L < \epsilon_L$, $\Delta a < \epsilon_a$ or $\Delta b < \epsilon_b$.

Figure 11:
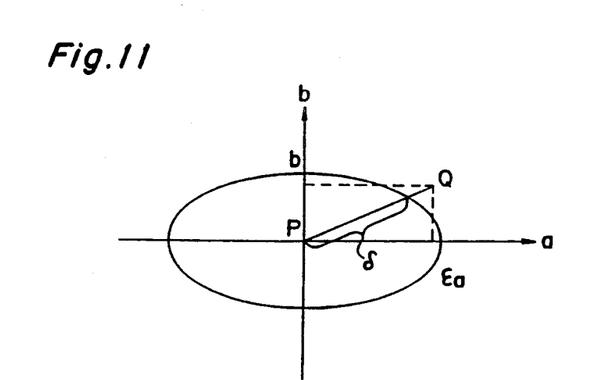
FIG. 11 shows an example in which it is judged there is a significant color difference.

For example, see FIG. 11. In this case, the measured point Q locates out of the elliptic defined by $\epsilon a$ and $\epsilon b$ although $\Delta a < \epsilon_a$ and $\Delta b < \epsilon_b$.

It is rather suitable to judge that there is a significant color different in such a case as mentioned above.

Thus, in this preferred embodiment, the length of the line segment PQ($=\Delta E$) is compared with a distance $\delta$ between the center P of the elliptic and a cross point of the elliptic with a line connecting points P and Q.

However, it is to be noted that the value of $\delta$ is determined by $\epsilon_L$, $\epsilon_a$, $\epsilon_b$, $\Delta L$, $\Delta a$ and $\Delta b$ and, accordingly, it is impossible to define only rule between $\Delta E$ and $\delta$.

The index f can be defined in the same manner as in the first preferred embodiment.

Figure 12:
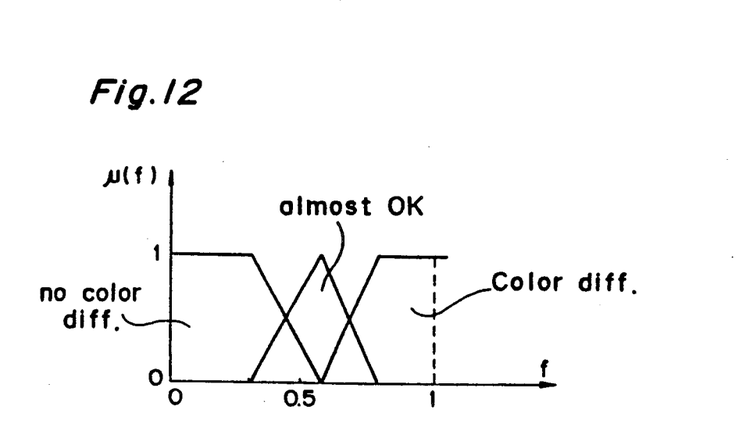
FIG. 12 shows an index function for determining whether or not there is a significant color difference.

But, it may be defined as shown in FIG. 12.

Simularly to the first preferred embodiment, the judgment for the color difference with use of Fuzzy inference was made and satisfactory results were obtained.

It is understood that various other modifications will be apparent to and can be readily made by those skilled in the art without departing from the scope and spirit of the present invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which the present invention pertains.

What is claimed is:

1. A method of judging whether the color difference between a color of an object and a reference color is substantial, said method comprising the steps of:

conveying the object to a color measurement station,
measuring said color of the object,
calculating a color difference between said color of the object and said reference color,
determining whether or not said color difference is within a predetermined range in which it is difficult to determine if said color difference is definite or negligible, and
judging whether or not said color difference is substantial, when it is within said predetermined range, with use of Fuzzy inference.

2. The method as claimed in claim 1, in which said predetermined range is determined according to said reference color.

3. The method as claimed in claim 1, in which the center $\epsilon_r$ of said predetermined range is determined by Fuzzy inference with rules formed from membership functions $\mu(L_0)$, $\mu(a_0)$, $\mu(b_0)$ and $\mu(\epsilon_r)$,
said rules being formulated in a general form of
{IF $\mu(L_0)$=Li, $\mu(a_0)$=ai, $\mu(b_0)$=bi; THEN $\mu(\epsilon_r)=\epsilon_i$}$_i^N=1$,
wherein $L_0$, $a_0$ and $b_0$ are L, a, b components of said reference color defined in L a b color space.

4. The method as claimed in claim 3, in which the center of said predetermined range is determined for each color component of said reference color in said color space.

5. The method as claimed in claim 4, in which each center of said predetermined range is determined by Fuzzy inference with rules of three kinds formulated in general forms as follows;
{IF $L_0^*$ is Li, $a_0^*$ is $a_i$, $b_0^*$ is $b_i$; THEN $\epsilon_L$ is $\epsilon_{Li}$}$_i^N=1$,
{IF $L_0^*$ is Li, $a_0^*$ is $a_i$, $b_0^*$ is $b_i$; THEN $\epsilon_a$ is $\epsilon_{ai}$}$_i^M=1$,
{IF $L_0^*$ is Li, $a_0^*$ is $a_i$, $b_0^*$ is $b_i$; THEN $\epsilon_b$ is $\epsilon_{bi}$}$_i^P=1$
(N, M, P, are arbitrary integers).

6. The method as claimed in claim 1, in which said Fuzzy inference is made with use of rules formulated in a general form as follows;
{IF $\mu(\Delta L)$ is $\Delta Li$, $\mu(\Delta a)$ is $\Delta ai$, $\mu(\Delta b)$ is $\Delta bi$; THEN $\mu(\Delta E)$ is $\epsilon_i$}$_i^N=1$,
wherein $\mu(X)$ is a membership function with a variant X, $$\Delta L = L - L_0, \Delta a = a - a_0, \Delta b = b - b_0 \text{ and}$$

$$\Delta E = \sqrt{(\Delta L)^2 + (\Delta a)^2 + (\Delta b)^2} ,$$

L, a and b are components of said color of an object in L a b color space and $L_0$, $a_0$ and $b_0$ are those of said reference color.

7. The method as claimed in claim 1, in which said Fuzzy inference is made with use of rules formulated in general forms as follows;
{IF $\Delta L$ is $\Delta Li$, $\Delta E$ is $\Delta Ei$; THEN f is fi}$_i^N=1$,
{IF $\Delta a$ is $\Delta ai$, $\Delta E$ is $\Delta Ei$; THEN f is fi}$_i^M=1$, and
{IF $\Delta b$ is $\Delta bi$, $\Delta E$ is $\Delta bi$; THEN f is fi}$_i^P=1$,
wherein $$\Delta L = L^* - L_0^*, \Delta a = a^* - a_0^*, \Delta b = b^* - b_0^*,$$

$$\Delta E = \sqrt{(\Delta L)^2 + (\Delta a)^2 + (\Delta b)^2} ;$$

$L^*$, $a^*$, $b^*$ are components of the color of an object measured in $L^*a^*b^*$ color space, $L_0^*$, $a_0^*$, $b_0^*$ are those of the reference color; and f is an index used for judging whether or not there is a substantial color difference.

8. A method as in claim 1, wherein said object is fabric.

9. A method as in claim 8, wherein said fabric is conveyed via conveyor rollers.

10. Apparatus for judging a color difference between a color an object and a reference color comprising;
means for entering color data of said reference color,
means for conveying the object to a color measurement station, said station including means for measuring said color of the object to obtain color data thereabout,
means for calculating a color difference between said color of the object and said reference color,
means for determining whether or not said color difference is within a predetermined range in which it is difficult to determine if said color difference is definite or negligible,
and means for judging whether or not said color difference is substantial, when it is within said predetermined range, with use of Fuzzy inference.

11. An apparatus as in claim 10, wherein said object is fabric.

12. An apparatus as in claim 11, wherein said means for conveying includes conveyor rollers along which the fabric is conveyed.

13. An apparatus as in claim 10, wherein said means for measuring color is a camera.

14. An apparatus as in claim 10, wherein said means for entering color data includes a keyboard operatively connected to a CPU.

* * * * *